(12) United States Patent
Finley et al.

(10) Patent No.: US 8,688,232 B2
(45) Date of Patent: Apr. 1, 2014

(54) MULTI-DUROMETER REINFORCED SUTURE SLEEVE

(75) Inventors: James Finley, Minneapolis, MN (US); Jesse Geroy, Ham Lake, MN (US); Lawrence Kane, Roseville, MN (US); John Swoyer, Blaine, MN (US)

(73) Assignee: Greatbatch Ltd., Clarence, NY (US)

( * ) Notice: Subject to any disclaimer, the term of this patent is extended or adjusted under 35 U.S.C. 154(b) by 92 days.

(21) Appl. No.: 13/445,204

(22) Filed: Apr. 12, 2012

(65) Prior Publication Data

US 2012/0330355 A1 Dec. 27, 2012

Related U.S. Application Data

(63) Continuation-in-part of application No. 13/164,942, filed on Jun. 21, 2011.

(51) Int. Cl.
*A61B 17/04* (2006.01)

(52) U.S. Cl.
USPC .......................................................... 607/116

(58) Field of Classification Search
None
See application file for complete search history.

(56) References Cited

U.S. PATENT DOCUMENTS

| | | |
|---|---|---|
| 4,516,584 A | 5/1985 | Garcia |
| 4,553,961 A | 11/1985 | Pohndorf et al. |
| 4,672,979 A | 6/1987 | Pohndorf |
| 5,273,053 A | 12/1993 | Pohndorf |
| 5,376,108 A | 12/1994 | Collins et al. |
| 5,484,445 A | 1/1996 | Knuth |
| 5,584,874 A | 12/1996 | Rugland et al. |
| 5,690,676 A | 11/1997 | Dipoto et al. |
| 5,814,021 A | 9/1998 | Balbierz |
| 5,843,146 A | 12/1998 | Cross, Jr. |
| 6,134,477 A | 10/2000 | Knuteson |
| 6,473,654 B1 | 10/2002 | Chinn |
| 6,685,728 B2 | 2/2004 | Sinnott et al. |
| 6,901,287 B2 | 5/2005 | Davis et al. |
| 6,932,834 B2 | 8/2005 | Lizardi et al. |
| 7,390,329 B2 | 6/2008 | Westra et al. |
| 7,824,421 B2 | 11/2010 | Weisenburgh et al. |
| 7,831,313 B2 | 11/2010 | Lauro |
| 2006/0264803 A1* | 11/2006 | Lui et al. .......................... 604/19 |
| 2007/0239242 A1 | 10/2007 | Graubert |
| 2008/0161890 A1* | 7/2008 | Lafontaine .................... 607/105 |
| 2008/0177304 A1* | 7/2008 | Westra et al. .................. 606/232 |
| 2008/0243151 A1 | 10/2008 | Binmoeller et al. |
| 2009/0248054 A1 | 10/2009 | Sage et al. |
| 2009/0287187 A1* | 11/2009 | Legaspi et al. ................. 604/523 |

(Continued)

FOREIGN PATENT DOCUMENTS

EP 0865799 9/1998

*Primary Examiner* — Carl H Layno
*Assistant Examiner* — Ankit Tejani
(74) *Attorney, Agent, or Firm* — Michael P. Horvath

(57) ABSTRACT

A suture anchor for securing a therapy delivery element in a desired location within a living body using a suture material. The suture anchor includes an inner sleeve with a primary lumen sized to receive the therapy delivery element. The inner sleeve includes a compliant material having a first durometer. An anchor body extends around at least a portion of the inner sleeve and includes a portion of the primary lumen. The anchor body includes a compliant material having a second durometer less than the first durometer. At least one exterior suture groove is located on the anchor body to receive the suture material. The exterior suture groove extends substantially to the inner sleeve so the suture material engages directly with the inner sleeve.

30 Claims, 11 Drawing Sheets

(56) References Cited

U.S. PATENT DOCUMENTS

| | | |
|---|---|---|
| 2010/0030311 A1 | 2/2010 | Lazeroms et al. |
| 2010/0049277 A1 | 2/2010 | Wahlstrand et al. |
| 2010/0076487 A1 | 3/2010 | Ilahi |
| 2010/0174240 A1 | 7/2010 | Wells et al. |
| 2010/0274336 A1 | 10/2010 | Nguyen-Stella et al. |
| 2012/0330354 A1* | 12/2012 | Kane et al. .................. 606/232 |

* cited by examiner

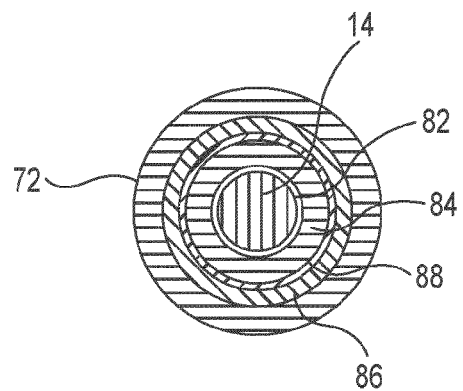 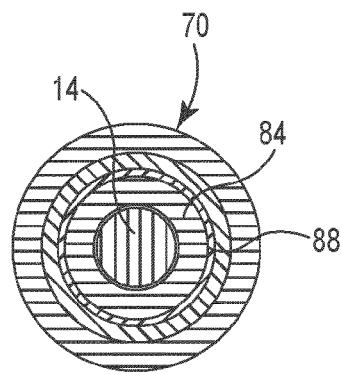
Fig. 7A  Fig. 7B
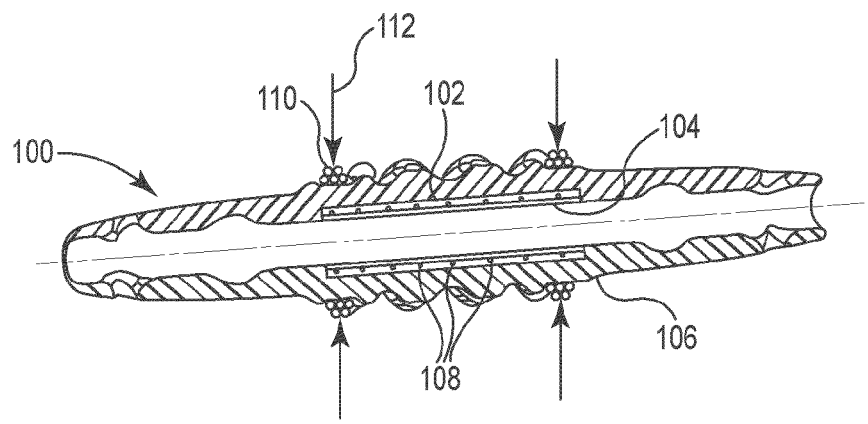
Fig. 8

MULTI-DUROMETER REINFORCED SUTURE SLEEVE

CROSS-REFERENCE TO RELATED APPLICATIONS

This application claims the benefit of U.S. application Ser. No. 13/164,942, filed Jun. 21, 2011, the disclosure of which is hereby incorporated by reference.

FIELD

The present disclosure relates to suture anchors for securing therapy delivery elements, such as stimulation leads or catheters, within a living body. The suture anchor includes an inner sleeve of a higher durometer material than the anchor body, and exterior suture grooves that extend substantially to the inner sleeve.

BACKGROUND

Implantable medical devices are used for a wide variety of medical conditions, such as for example, cardiac pacing and sensing, cardiac rhythm management, treatments for congestive heart failure, implanted defibrillators, and neurostimulation. Neurostimulation encompasses a wide range of applications, such as for example, pain control, nervous tremor mitigation, incontinent treatment, epilepsy seizure reduction, and vagus nerve stimulation for clinical depression. These implantable medical devices generally include an implanted pulse generator that generates electrical pulses or signals that are transmitted to a targeted tissue or nerves through a therapy delivery element, such as a lead with electrodes.

Controlled placement of the therapy delivery element is required for improved therapeutic efficacy or reduced side effects. Retaining the implanted therapy delivery element in the desired location also creates difficulties because the location may change over time as the patient moves. Anchors typically form a mechanical resistance lock that prevents the therapy delivery element from sliding around as the patient moves. In most configurations, anchors consist of a metal insert housed inside of a silicone sleeve and function by using suture knots to collapse the insert onto the lead. A variety of anchors are available to prevent the therapy delivery element from migrating away from a specifically selected stimulation site.

Clinicians inserting and anchoring leads typically prefer to perform the procedure rapidly, in a minimally invasive manner, and fix the lead in a manner that reduces the opportunity for the lead to migrate if practicable. Examples of some previous anchors are shown in U.S. Pat. No. 6,134,477 "Adjustable Medical Lead Fixation System" by Knuteson (Oct. 17, 2000); U.S. Pat. No. 5,484,445 "Sacral Lead Anchoring System" by Knuth (Jan. 16, 1996); and, U.S. Pat. No. 5,843,146. "Adjustable Medical Lead Anchor" by Cross, Jr. (Dec. 1, 1998).

U.S. Pat. No. 4,553,961 (Pohndorf et al.) discloses a typical suture sleeve with an outer elastomeric sleeve and an inner gripping structure. The lead is inserted though a lumen in the anchor. The gripping structure is radially compressed by the surgeon tying a suture material around the suture sleeve. The suture material causes the outer elastomeric sleeve to compress the inner gripping structure, which then collapses onto and grips the lead.

An issue with such anchors is that the elastomeric sleeve (typically silicone) may be too thick and prevents the insert from fully closing. In most cases, failure to secure the lead is due to the silicone absorbing most of the compressive force applied by the sutures, or the sleeve getting caught in the gaps of the insert as it closes. This problem will become a larger issue as leads become more flexible in the future. Essentially, as leads become more flexible they will tend to neck down when stretched, causing the overall diameter of the lead to decrease. Since these anchors function by a resistance lock, the holding force is greatly reduced as the lead necks down. As a result, anchors will have to collapse further in order to maintain a high holding force. If the sleeve interferes with compression of the insert, lead migration can result.

BRIEF SUMMARY

The present disclosure is directed to a suture anchor for securing a therapy delivery element in a desired location within a living body using a suture material. The suture anchor includes an inner sleeve with a primary lumen sized to receive the therapy delivery element. The inner sleeve includes a compliant material having a first durometer. An anchor body extends around at least a portion of the inner sleeve and includes a portion of the primary lumen. The anchor body includes a compliant material having a second durometer less than the first durometer. At least one exterior suture groove is located on the anchor body to receive the suture material. The exterior suture groove extends substantially to the inner sleeve so the suture material engages directly with the inner sleeve. The first durometer is preferably a shore hardness ranging between about 65 to about 105, between about 75 to about 95, or between about 80 to about 90 silicone measured according to ASTM D2240 type A. The second durometer is preferably a shore hardness ranging between about 30 to about 80, between about 40 to about 70, or between about 50 to about 60 silicone measured according to ASTM D2240 type A.

In another embodiment, the inner sleeve includes an outer layer of a material having the first durometer and an inner layer of a material having a third durometer less than the first durometer. A reinforcing structure is optionally integrated with the inner sleeve. The reinforcing structure can be one of a coil, a braid, a tube, or a woven component.

The suture anchor preferably includes a deformable insert located in the primary lumen of the inner sleeve. The insert includes a plurality of beams connected at deflection regions adapted to deform in response to a radially inward force applied around the suture grooves by the suture material. The insert is preferably a material that plastically deforms in response to the radially inward force. In one embodiment, the insert includes a pair of fixed rings located at opposite ends of the insert. At least one beam directly connects the fixed rings and a plurality of beams indirectly connect the fixed rings.

The suture material located in the suture groove is tensioned to apply a radial compression force that engages inner sleeve with the therapy delivery element. The inner sleeve spreads the radial compression force along a greater surface area of the therapy delivery element. In one embodiment, the suture material is configured in a self-locking compression knot located in the suture groove. Distal ends of the suture material are adapted to receive a tension force that is transmitted as a radial compression force to deform the inner sleeve to engage with the therapy delivery element.

The present disclosure is also directed to a neurostimulation system including an implantable pulse generator and a therapy delivery element with a proximal end adapted to electrically couple with the implantable pulse generator and a distal end with a plurality of electrodes electrically coupled to the implantable pulse generator. The present suture anchor secures the therapy delivery element in a desired location within a living body. A suture material located in the suture grooves applies a radial compression force that engages inner sleeve with the therapy delivery element.

The present disclosure is also directed to a method of securing a therapy delivery element at a desired location within a living body. The method includes the steps of inserting the therapy delivery element through a primary lumen of an inner sleeve of a suture anchor. The suture anchor includes an anchor body extending around at least a portion of the inner sleeve. The inner sleeve is a compliant material having a first durometer and the anchor body is a compliant material having a second durometer less than the first durometer. The anchor is slid along the therapy delivery element to the desired location. A suture material is wrapped around at least one exterior suture groove in the anchor body such that the suture material engages directly with the inner sleeve. A tension force is applied to distal ends of the suture material that transmits a radial compression force to engage the inner sleeve with the therapy delivery element.

The present disclosure is also directed to a method of implanting a neurostimulation system within a living body. The method comprising the steps implanting an implantable pulse generator within the living body. Electrodes at a distal end of a therapy delivery element are positioned at a target location within the living body. A suture anchor according to the present disclosure is slide along the therapy delivery element to the desired location. A suture material is wrapped around at least one exterior suture groove in the anchor body such that the suture material engages directly with the inner sleeve. A tension force is applied to distal ends of the suture material that transmits a radial compression force to engage the inner sleeve with the therapy delivery element. Proximal ends of the therapy delivery element are electrically coupled to the implantable pulse generator.

BRIEF DESCRIPTION OF THE SEVERAL VIEWS OF THE DRAWINGS

FIG. 7A is a sectional view of the suture anchor of FIG. 4 before the suture material is tensioned.

FIG. 7B is a sectional view of the suture anchor of FIG. 4 after the suture material is tensioned.

FIG. 8 is a sectional view of an alternate suture anchor with a multi-durometer inner sleeve and a pre-tied suture material in accordance with an embodiment of the present disclosure.

DETAILED DESCRIPTION OF SOME EMBODIMENTS

The description that follows relates to a spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof "Target tissue site" refers generally to the target site for implantation of a therapy delivery element, regardless of the type of therapy.

Figure 1:
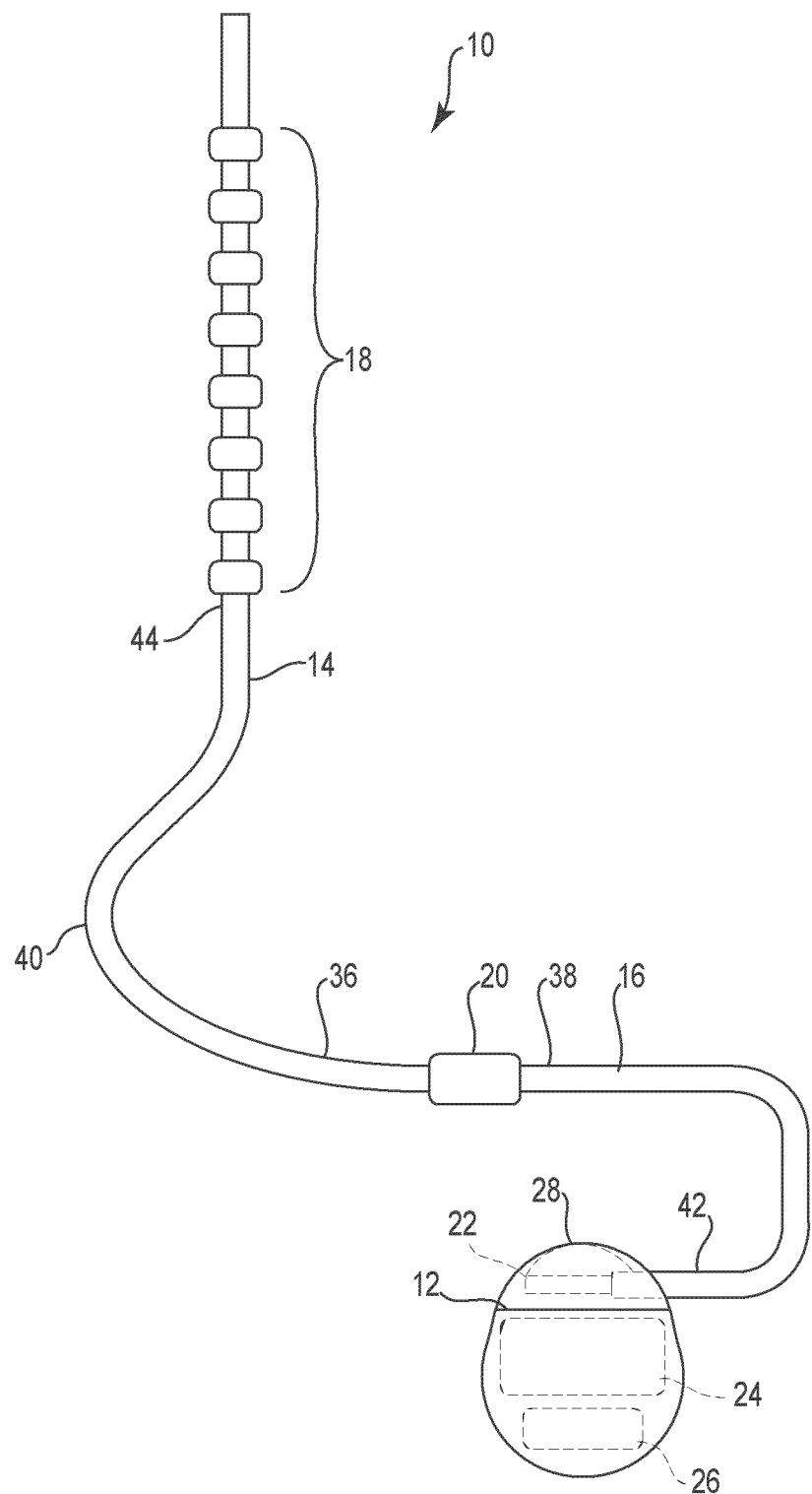
FIG. 1 is a schematic illustration of a therapy delivery system.

FIG. 1 illustrates a generalized therapy delivery system 10 that may be used in spinal cord stimulation (SCS), as well as other stimulation applications. The therapy delivery system 10 generally includes an implantable pulse generator 12, an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes elongated body 40 having a proximal end 36 and a distal end 44. The elongated body 40 typically has a diameter of between about 0.03 inches to 0.07 inches and a length within the range of 30 cm to 90 cm for spinal cord stimulation applications. The elongated body 40 may be composed of a suitable electrically insulative material, such as, a polymer (e.g., polyurethane or silicone), and may be extruded as a uni-body construction.

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 are protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2:
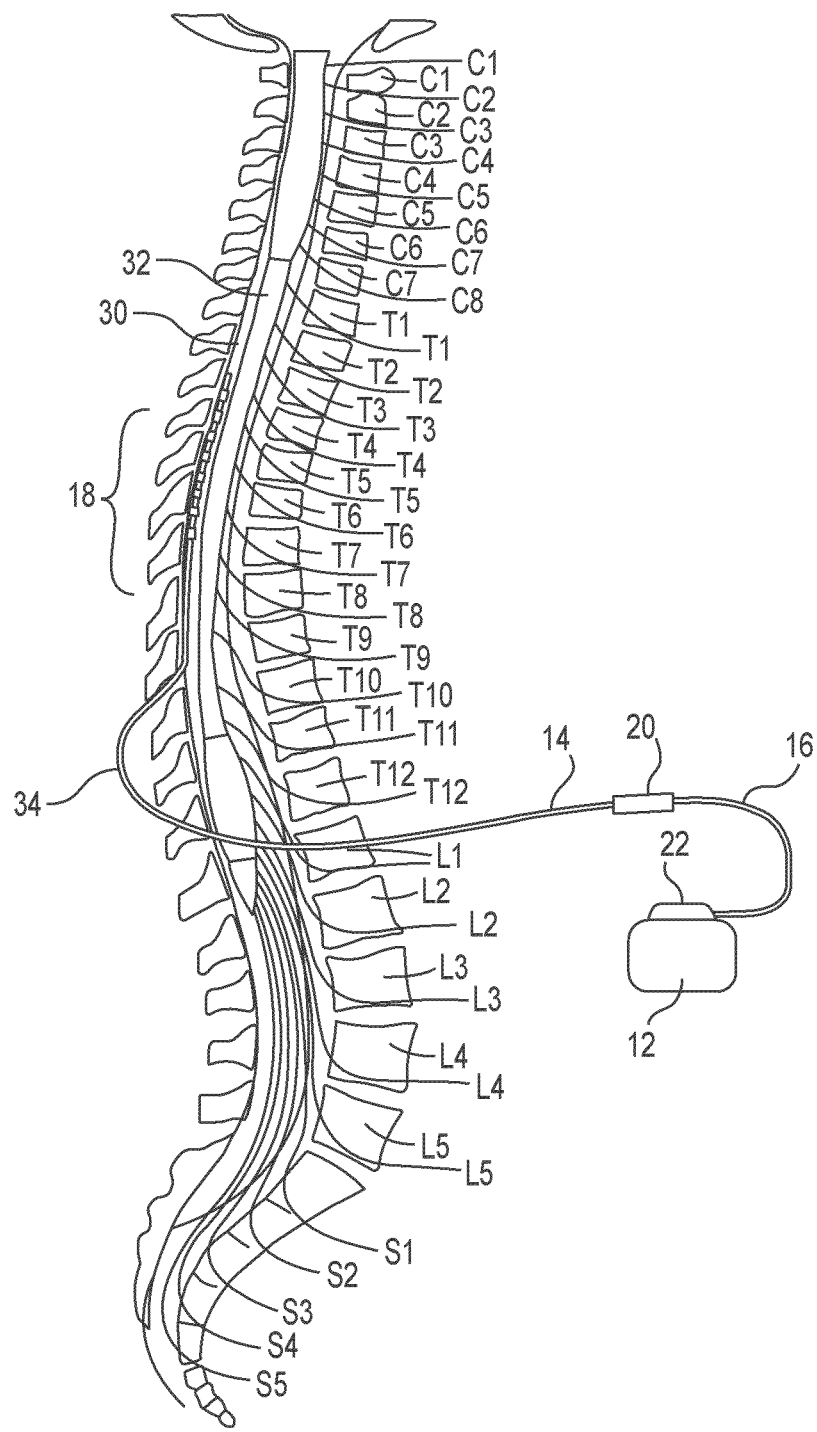
FIG. 2 is a schematic illustration of an environment for a therapy delivery system in accordance with an embodiment of the present disclosure.

FIG. 2 illustrates the therapy delivery element 14 implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as for example proximate the sacral nerves.

Figure 3:
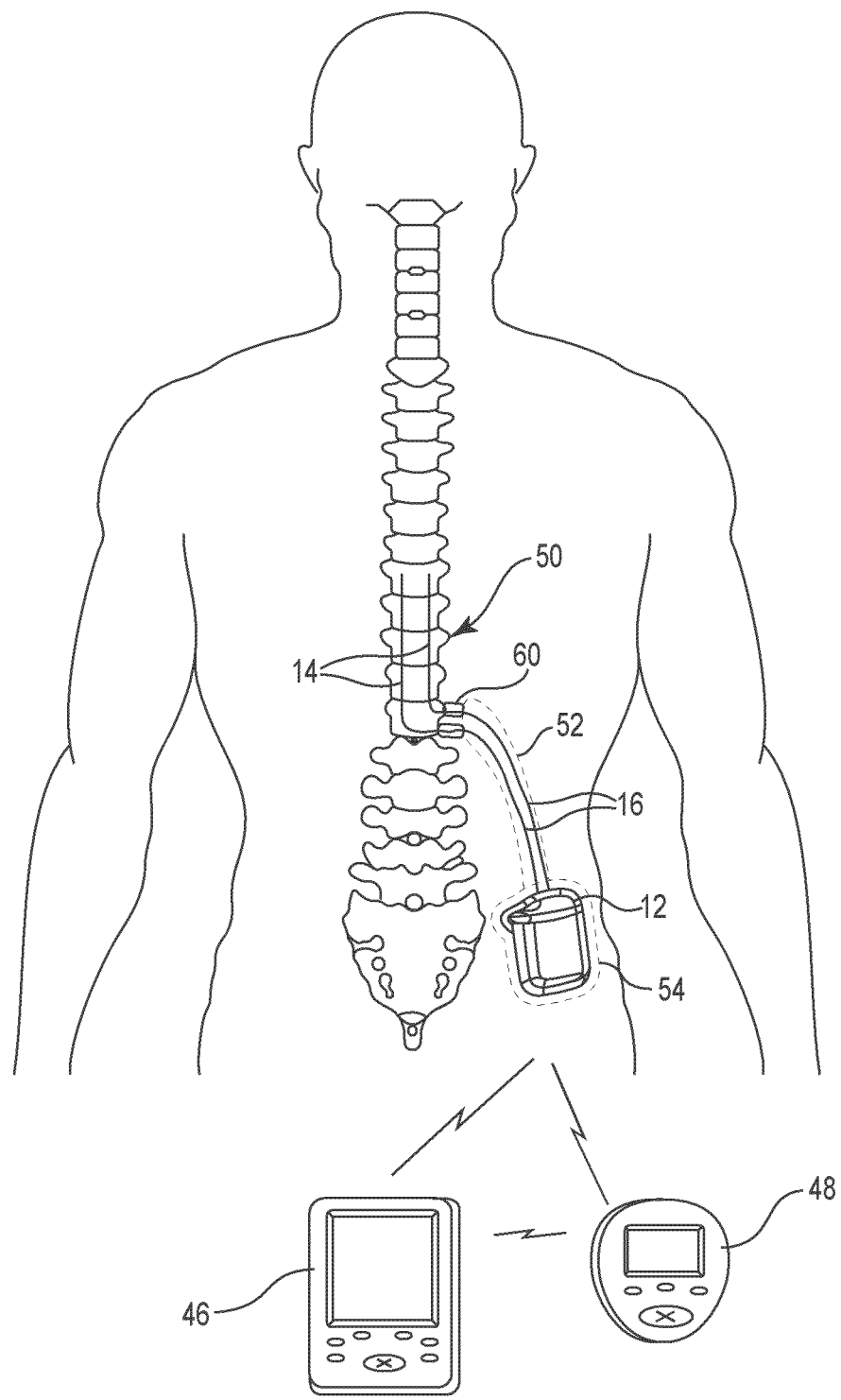
FIG. 3 is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 3. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 3, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

FIG. 3 also illustrates a general environment that may benefit from use of a tunneling tool in accordance with an embodiment of the present disclosure. Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" are used interchangeably, unless content clearly dictates otherwise.

The therapy delivery elements 14 are typically fixed in place near the location selected by the clinician using the present suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner.

Figure 4:
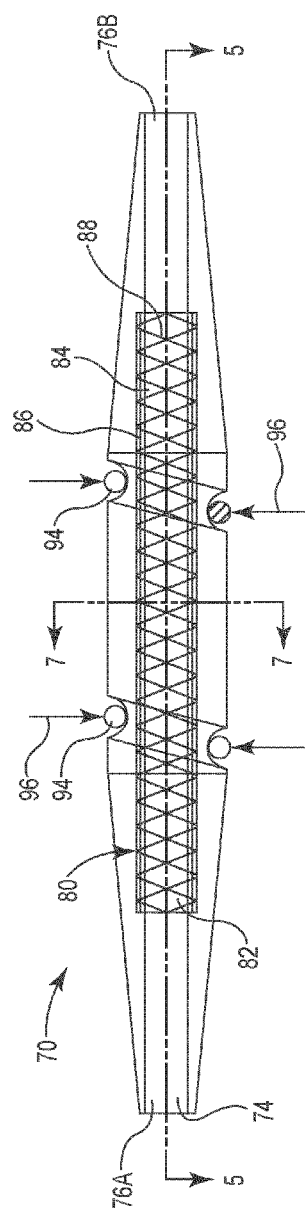
FIG. 4 is a sectional view of a suture anchor for a therapy delivery element with a multi-durometer inner sleeve in accordance with an embodiment of the present disclosure.
Figure 5:
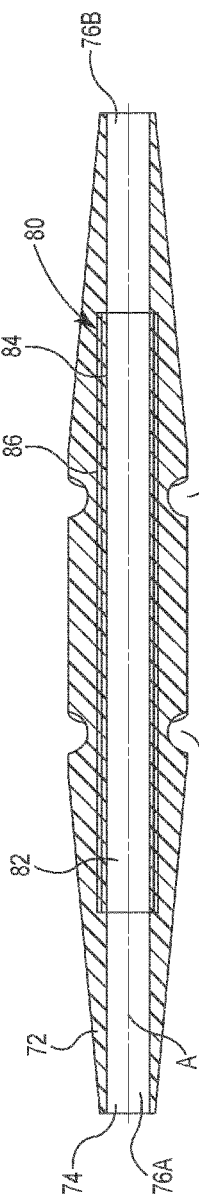
FIG. 5 is an alternate sectional view of the suture anchor of FIG. 4.
Figure 6:
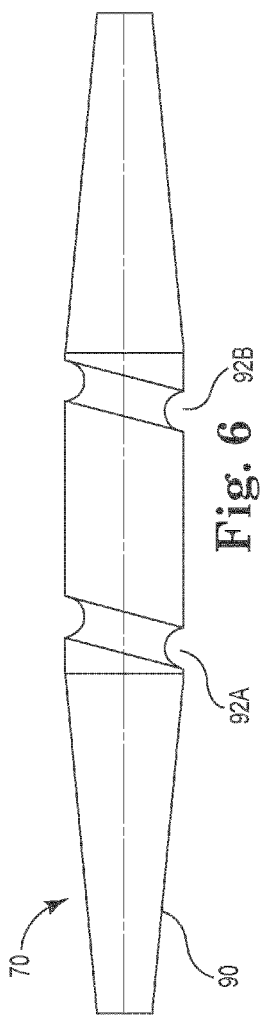
FIG. 6 is a side view of the suture anchor of FIG. 4.

FIGS. 4 through 6 are various views of a suture anchor 70 with a multi-durometer inner sleeve 80 in accordance with an embodiment of the present disclosure. Anchor body 72 includes primary lumen 74 extending along axis A from first opening 76A to second opening 76B ("76"). The anchor body 72 is preferably constructed from a medical grade elastomeric material, such as for example, silicone rubber or polyurethane/silicone blends.

The inner sleeve 80 is located in the primary lumen 74. Inner sleeve lumen 82 is aligned and co-linear with primary lumen 74. The primary lumen 74 and inner sleeve lumen 82 preferably have a larger diameter than outside diameter of therapy delivery element 14 to permit easy positioning of the suture anchor 70. FIG. 7A is a cross section of the suture anchor 70 before compressive force 96 is applied. FIG. 7B is a cross section of the suture anchor 70 after compressive force 96 is applied.

The inner sleeve 80 is constructed from at least two different durometer materials. Inner layer 84 of the inner sleeve 80 is constructed from a softer, more pliable material that easily conforms to the outside diameter of the therapy delivery element 14 to reduce slippage. The inner layer 84 preferably has a shore hardness measured according to ASTM D2240 type A ranging between about 25 to about 30, between about 20 to about 35, or between about 15 to about 40. Outer layer 86 of the inner sleeve 80 is a harder, stiffer durometer material that protects the therapy delivery elements 14 from damage due to over-tightening the tie down sutures. The outer layer 86 preferably has a shore hardness ranging between about 65 to about 75, between about 60 to about 80, or between about 50 to about 90. The inner and outer layers 84, 86 can be constructed from a variety of biocompatible materials, such as for example silicone rubber, polyurethane, nylon, polyester, or polyimide.

Reinforcing structure 88 is preferably located generally between the inner and outer layers 84, 86 of the inner sleeve 80. The reinforcing structure 88 can be constructed from metal or an implantable grade polymer, such as for example, Dacron, polyurethane, nylon, polyester, polyimide, and the like. The reinforcing structure 88 can be configured as a coil, braid, tube, woven component, or a variety of other configurations suitable to protect the therapy delivery element 14. In another embodiment, the reinforcing structure 88 can be integrated with the inner sleeve 80 using a variety of techniques, such as for example, by overmolding, extruding, or co-extruding the inner and/or outer layers 84, 86 onto the reinforcing structure 88.

Outer surface 90 of the suture body 72 includes one or more grooves 92A, 92B ("92") adapted to receive a compressive member, such as for example, suture material 94. In the illustrated embodiment, the grooves 92 are oriented at an angle with respect to the reinforcing structure 88 to provide further protection for the therapy delivery element 14.

As best illustrated in FIG. 7B, tensioning the suture material 94 applies a compressive force 96 on the suture anchor 70 so that inner layer 84 of the inner sleeve 80 contacts the therapy delivery element 14. The low durometer inner layer 84 conforms to the outer surface of the therapy delivery element 14. The inner layer 84 can be made from any of the medical grade elastomeric material noted herein, including, silicone rubber or polyurethane/silicone blends. Reinforcing structure 88 protects the therapy delivery element 14 from over-tightening. The compressive force 96 is concentrated under the suture material 94, while the reinforcing structure 88 serves to spread radial compression force 96 along a greater surface area of the therapy delivery element 14.

FIG. 8 illustrates an alternate suture anchor 100 with an inner sleeve 102 in accordance with an embodiment of the present disclosure. The inner sleeve 102 includes inner layer 104 constructed from a softer, more pliable material and outer layer 106 constructed from a harder, stiffer durometer material. The inner layer 104 and outer layer 106 can be constructed from a variety of materials, such as for example, Dacron, polyurethane, nylon, polyester, polyimide, and the like. Reinforcing structure 108 is preferably located between the inner and outer layers 104, 106.

Suture material 110 is preferably configured as a pre-tied, self-locking compression knot, such as for example, a nail knot. Using a nail knot spreads the radial compression force 112 over a larger surface of the anchor sleeve 100, increasing frictional engagement between the inner layer 104 and the therapy delivery element 14. The reinforcing structure 108 reduces damage to the suture anchor 100. The pre-tied knot removes variation out of the process by requiring all surgeons to use the same suture material 110 and the same pre-tied knot. As used herein, "compression knot" refers to one or more loops of suture material that contracts when one or more distal ends of the suture material are tensioned. "Self-locking" refers to a knot that relies on friction between the suture material to substantially maintain a radially compressive force on a structure.

Figure 9:
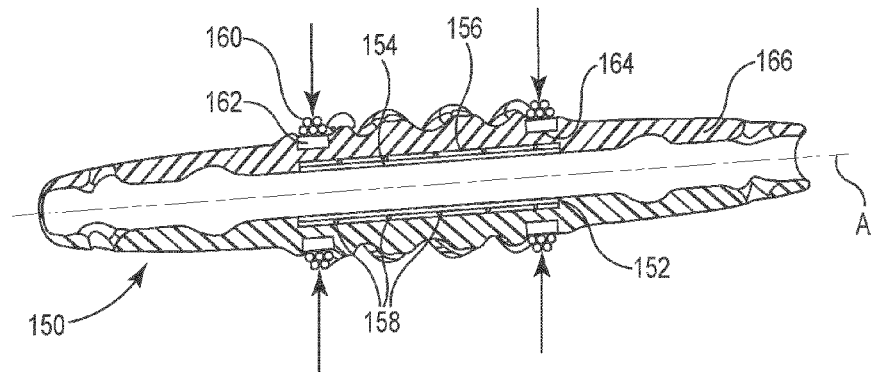
FIG. 9 is a sectional view of an alternate suture anchor with a multi-durometer inner sleeve and compression members in accordance with an embodiment of the present disclosure.

FIG. 9 illustrates an alternate suture anchor 150 with an inner sleeve 152 in accordance with an embodiment of the present disclosure. The inner sleeve 152 includes inner layer 154 constructed from a softer, more pliable material and outer layer 156 constructed from a harder, stiffer durometer material. Reinforcing structure 158 is preferably located between the inner and outer layers 154, 156.

Suture material 160 is wrapped around compression members 162. The compression members 162 are preferably recessed in the compression grooves 164 to retain the suture material 160 in the desired axial location along axis A. The compression members 162 are optionally attached to anchor body 166, such as for example, using medical adhesive, liner, mechanical interlocks and the like.

The compression members 162 can be a one-piece structure, such as for example a C-shaped band or a variety of multi-piece structure. The compression members 162 can be any rigid or semi-rigid material, such as for example, a thermoplastic or thermoset material, stainless steel, Nitinol, or a combination thereof. In another embodiment, the compression members 162 are radiopaque to facilitate medical imaging.

Figure 10A:
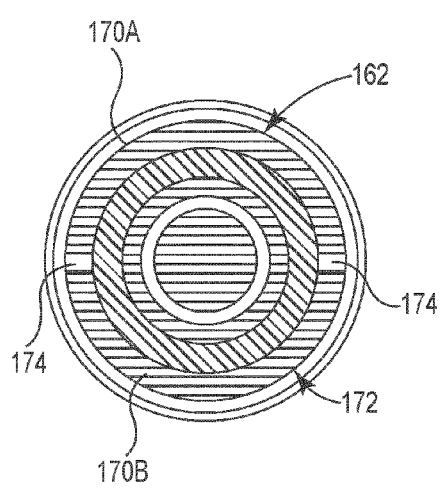
FIG. 10A is a sectional view of the suture anchor of FIG. 9 before the suture material is tensioned.

As best illustrated in FIG. 10A, the compression members 162 include an upper portion 170A and a lower portion 170B ("170") shown in an open configuration 172. The compression members 162 are preferably discontinuous. For example, in the illustrated embodiment, the compression members 162 include compression gaps 174.

Figure 10B:
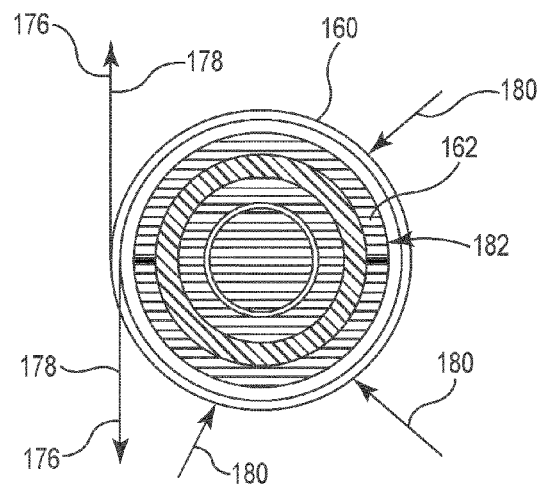
FIG. 10B is a sectional view of the suture anchor of FIG. 9 after the suture material is tensioned.

As best illustrated in FIG. 10B, tension force 176 is applied to distal ends 178 of the suture material 160, which generates radial compression force 180 that is applied to the compression members 162. The upper and lower portions 170 of the compression members 162 are displaced radially inward by the force 180 until edges engage in compressed configuration 182. The discontinuous nature of the compression members 162 permits the compression gaps 174 to be closed to form the compressed configuration 182. Embodiments of the suture anchor with the present compression members 182 can be used with or without the reinforcing structure in the inner sleeve 152.

In another embodiment, the suture anchor can be infused with medical adhesive in accordance with an embodiment of the present disclosure. The medical adhesive is preferably delivered after the anchor is positioned in the desired location along the therapy delivery element 14.

The medical adhesive can be any type of biocompatible medical-grade adhesive. Such medical adhesive includes polyurethane and/or silicone adhesives. One example is Room Temperature Vulcanization (RTV) silicone adhesive which cures at room temperature. This type of adhesive is generally kept under pressure to prevent it from curing until ready to use. When pressure is removed (e.g., the adhesive is dispensed from the tube) the adhesive will set up, becoming solid, or semi-solid in nature. Another example is a silicone or polyurethane adhesive that cures when exposed to UV or visible light, as is available from the Dymax Corporation.

Figure 11A:
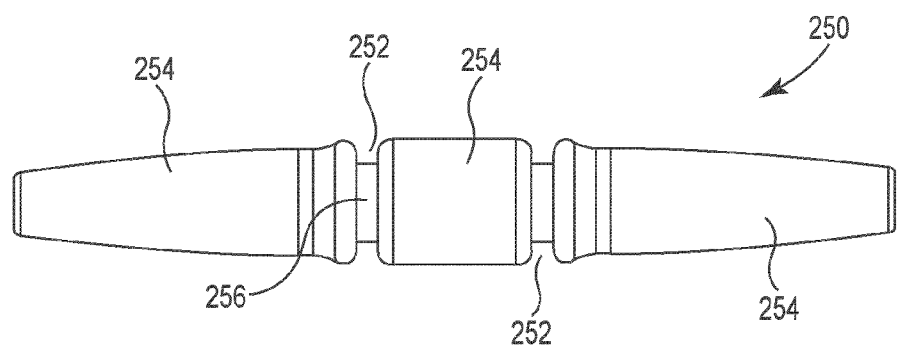
FIGS. 11A-11C illustrate an alternate suture anchor with a high durometer inner sleeve in accordance with an embodiment of the present disclosure.
Figure 11B:
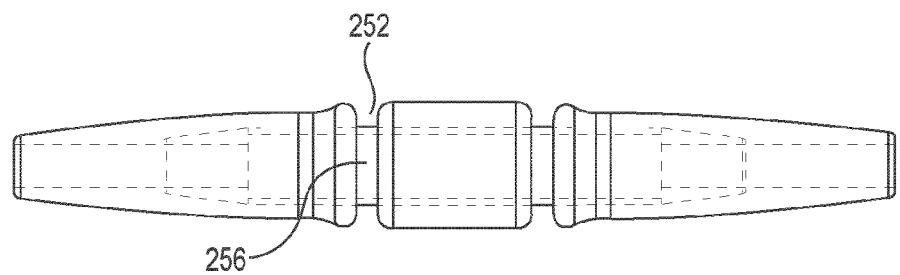
Figure 11C:
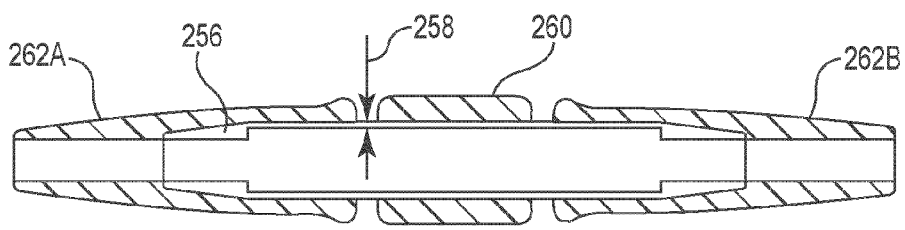

FIGS. 11A-11C illustrate an alternate suture anchor 250 with channels 252 adjacent thin walled insert 256 in accordance with an embodiment of the present disclosure. The channels 252 serve as guides for where the suture material (see e.g., FIG. 4) is tied to collapse the suture anchor 250 onto the therapy delivery element. The channels 252 also serve to prevent the lower durometer anchor body 254 from interfering with the radially compressive force generated by the suture material.

During the implantation procedure, the doctor situates the suture anchor 250 on the therapy delivery element and tightens it down using one or more suture knots tied around the channels 252 adjacent the inner sleeve 256. Wall thickness 258 of the inner sleeve 256 proximate the channels 252 is relatively thin to facilitate engagement with the therapy delivery element. In the illustrated embodiment, the wall thickness 258 is in the range of about 0.010 inches to about 0.012 inches for an inner sleeve 256 constructed from biomedical silicone having a shore hardness of about 80, measured according to ASTM D2240 type A.

Reducing the wall thickness 258 of the inner sleeve 256 increases the risk of tearing. Some possible sources of these tears include the initial compression of the silicone over sharp edges of an insert, a doctor cutting too far when trying to remove a suture, or continual motion and stress the anchor is subjected to as the patient moves around. If a tear propagates through the suture anchor 250 it possible for an insert (see e.g., FIG. 12) to damage the therapy delivery element. The inner sleeve 256 is preferably constructed from a higher durometer material than anchor body 254 to reduce the risk of tearing the inner sleeve 256. In one embodiment, the inner sleeve 256 is constructed from about shore hardness ranging between about 65 to about 105, between about 75 to about 95, or between about 80 to about 90 silicone measured according to ASTM D2240 type A. In another embodiment, the inner sleeve 256 includes a reinforcing structure such as illustrated in FIG. 4 to reduce the risk of tears propagating.

The present suture anchor 250 is optionally constructed using a two-step process. First, the higher durometer inner sleeve 256 is molded or extruded and cut to length. Second, the anchor body 254, including for example central divider 260 and strain relief ends 262A, 262B, is overmolded onto the inner sleeve 256 using a lower durometer material, such as for example, a silicone material with a shore hardness ranging between about 30 to about 80, between about 40 to about 70, or between about 50 to about 60 measured according to ASTM D2240 type A. The lower durometer anchor body 254 maintains the soft outer surface and overall mobility of current anchor sleeves.

Figure 12:
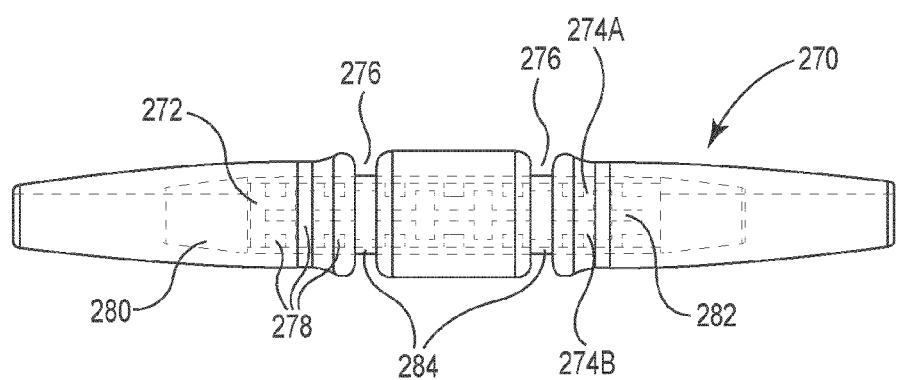
FIG. 12 illustrates an alternate suture anchor with a high durometer inner sleeve containing an insert in accordance with an embodiment of the present disclosure.
Figure 13A:
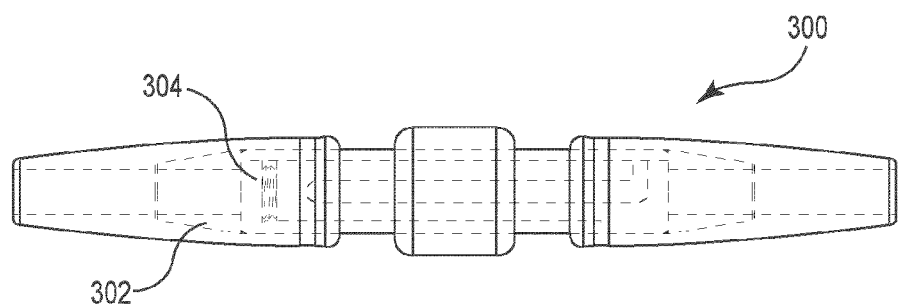
FIG. 13A illustrates alternate suture anchor with a high durometer inner sleeve and an insert in accordance with an embodiment of the present disclosure.
Figure 13B:
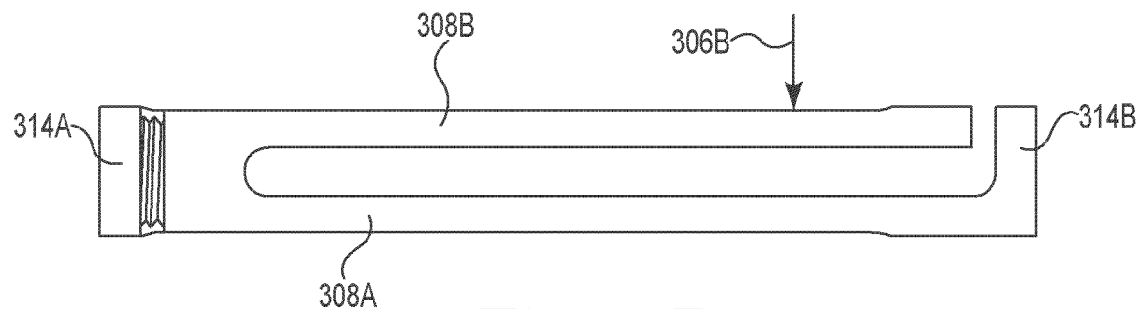
FIGS. 13B-13D illustrate various view of the insert of FIG. 13A.
Figure 13C:
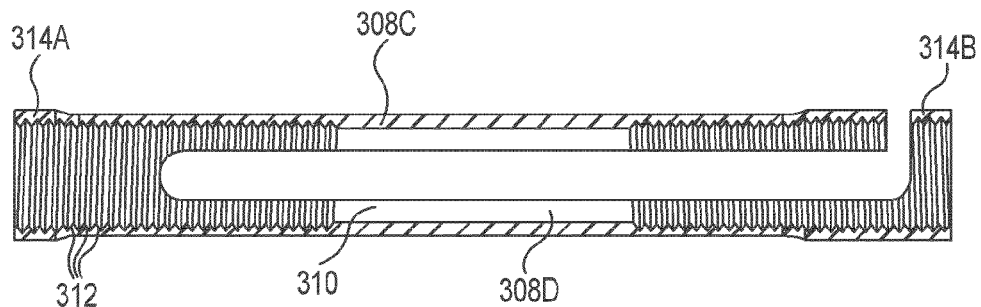
Figure 13D:
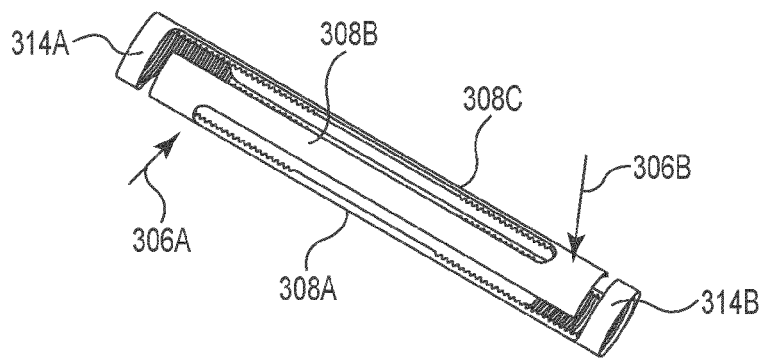

FIG. 12 illustrates a variation of the suture anchor 270 with collapsible insert 272 located in inner sleeve 280 in accordance with an embodiment of the present disclosure. The insert 272 preferably includes a plurality of beams 274A, 274B ("274") designed to deflect or deform when a radially compressive force is applied by a suture material located in channels 276. Deflection of the insert 272 can be one or more of linear or rotary displacement, bending, twisting, or a combination thereof. The deflection preferably encompasses multiple degrees of freedom.

In the illustrated embodiment, the beam 274 includes a plurality of locations of weakness 278 that facilitate localized deformation. The localized deformation is preferably plastic, but can also be elastic, or a combination of elastic and plastic deformation. As used herein, "location of weakness" refers to any discontinuity in a beam structure that facilitates localized deformation, such as for example, slits, holes, recesses, regions thinning, and the like.

The insert 272 can be made from a variety of plastically and/or elastically deformable materials, such as for example, nylon, stainless steel, Nitinol, and the like. In another embodiment, the insert 272 includes radiopaque properties. In one embodiment, the insert 272 is stainless steel formed by wire electro-discharge machining processes. Alternate inserts for use in the present disclosure are set forth in commonly assigned U.S. patent application Ser. No. 13/045,947 entitled Anchor Sleeve for Implantable Lead, filed Mar. 11, 2011, which is hereby incorporated by reference.

In one embodiment, the inner sleeve 280 is expanded using Heptane and positioned over the insert 272. As the Heptane evaporates the silicone recedes to its original size fully capturing the insert 272 within the inner sleeve 280.

The thinner walls 284 of the inner sleeve 280 reduce the risk of the inner sleeve 280 interfering with the collapse of gaps 282 of the insert 272 during engagement of the suture anchor 270 with a therapy delivery element. The thin walls 284 of the inner sleeve 280 help to reduce the absorption of the suture's compressive force. As a result, the insert 272 is allowed to collapse and produce the strongest holding force possible against the therapy delivery element. For this reason, the present suture anchor 270 is able to outperform current anchor sleeves and will be the better option as leads become more flexible in the future. In one embodiment, the insert 272 limits the total compression of the suture anchor 270, such as the compression members discussed above.

FIGS. 13A through 13D illustrate a suture anchor 300 with an inner sleeve 302 containing an alternate insert 304 in accordance with an embodiment of the present disclosure. The insert 304 includes a pair of fixed rings 314A, 314B ("314") and four beams 308A, 308B, 308C, 308D ("308"). The fixed rings 314 are directly connected by beam 308D, while the beams 308A, 308B, 308C form a serpentine structure that indirectly connects the fixed rings 314.

The beams 308A, 308B are configured to move in direction 306A, and beams 308B, 308C are configured to move in direction 306B. In the illustrated embodiment, inside surface 310 of the insert 304 includes a plurality of ridges or threads 312 that facilitate engagement with a therapy delivery element.

The fixed rings 314 help to keep the insert 304 from slipping out of the inner sleeve 302 when the anchor 300 is put under a tensile load. Also, since the rings 314 include threads 312, they help to grip the underlying lead if the anchor 300 tips or is put under tension at an angle. For example, anchors often assume an angled orientation when subjected to tensile load above about 1 pound. The larger the load, the larger the angle the anchor assumes.

Figure 14:
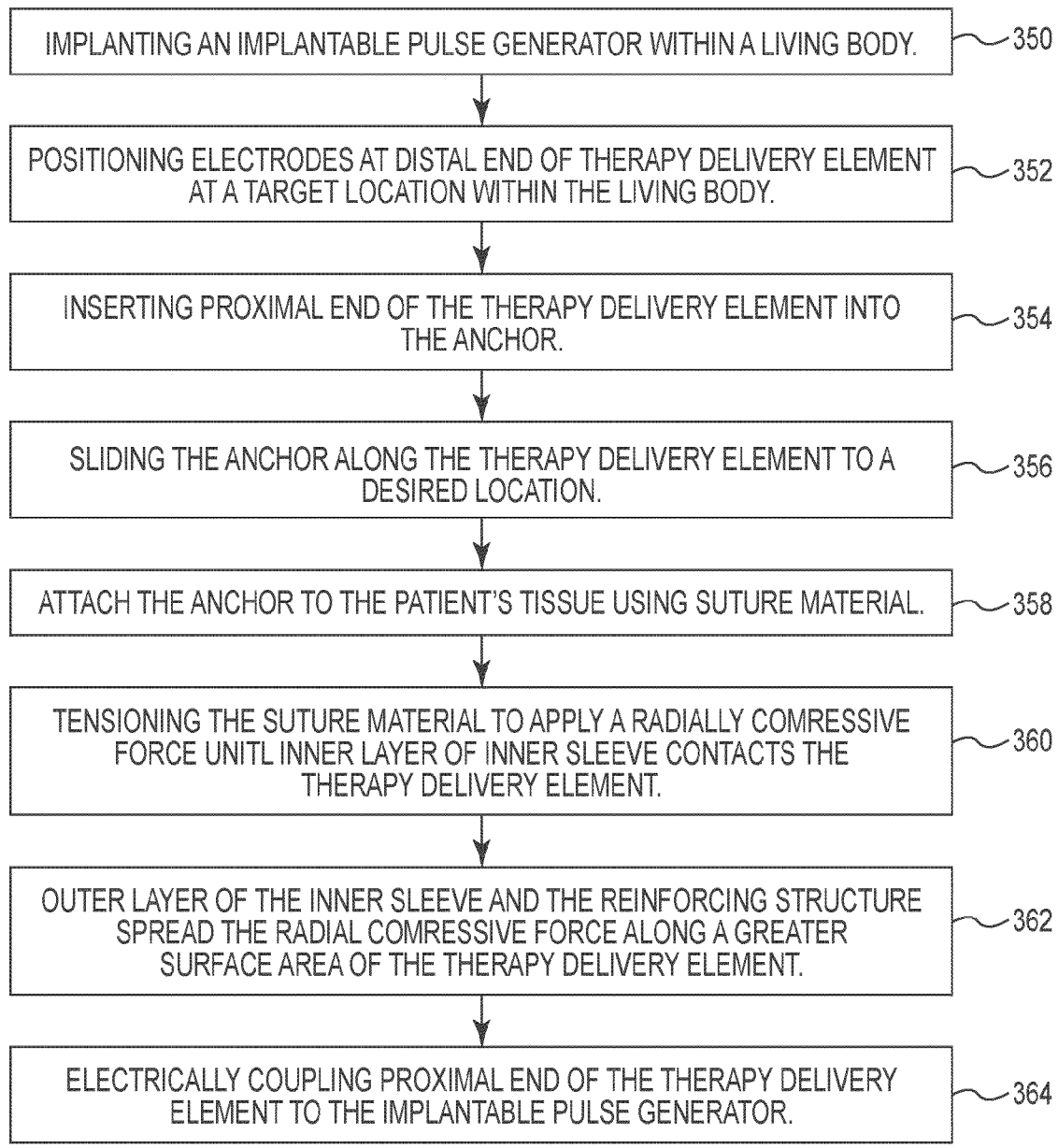
FIG. 14 is a flow diagram of a method of implanting a neurostimulation system within a living body in accordance with an embodiment of the present disclosure.

FIG. 14 is a flow diagram of a method of implanting a neurostimulation system within a living body. The method includes the steps of implanting an implantable pulse generator within the living body (350). Electrodes at a distal end of a therapy delivery element are positioned at a target location within the living body (352). A proximal end of the therapy delivery element is inserted into a lumen in the present suture anchor (354). The suture anchor is slid along the therapy delivery element in a desired location (356). The surgeon then attaches the suture anchor to the patient's tissue, such as for example, using staples or external sutures wrapped around central ribs of the suture anchor (358). Suture material wrapped around the suture anchor is tensioned to apply a radial compression force until inner layer of inner sleeve contacts the therapy delivery element (360). Outer layer of the inner sleeve and the reinforcing structure spreads the radial compression force along a greater surface area of the therapy delivery element (362). The proximal end of the therapy delivery element is electrically coupled to the implantable pulse generator (364).

Figure 15:
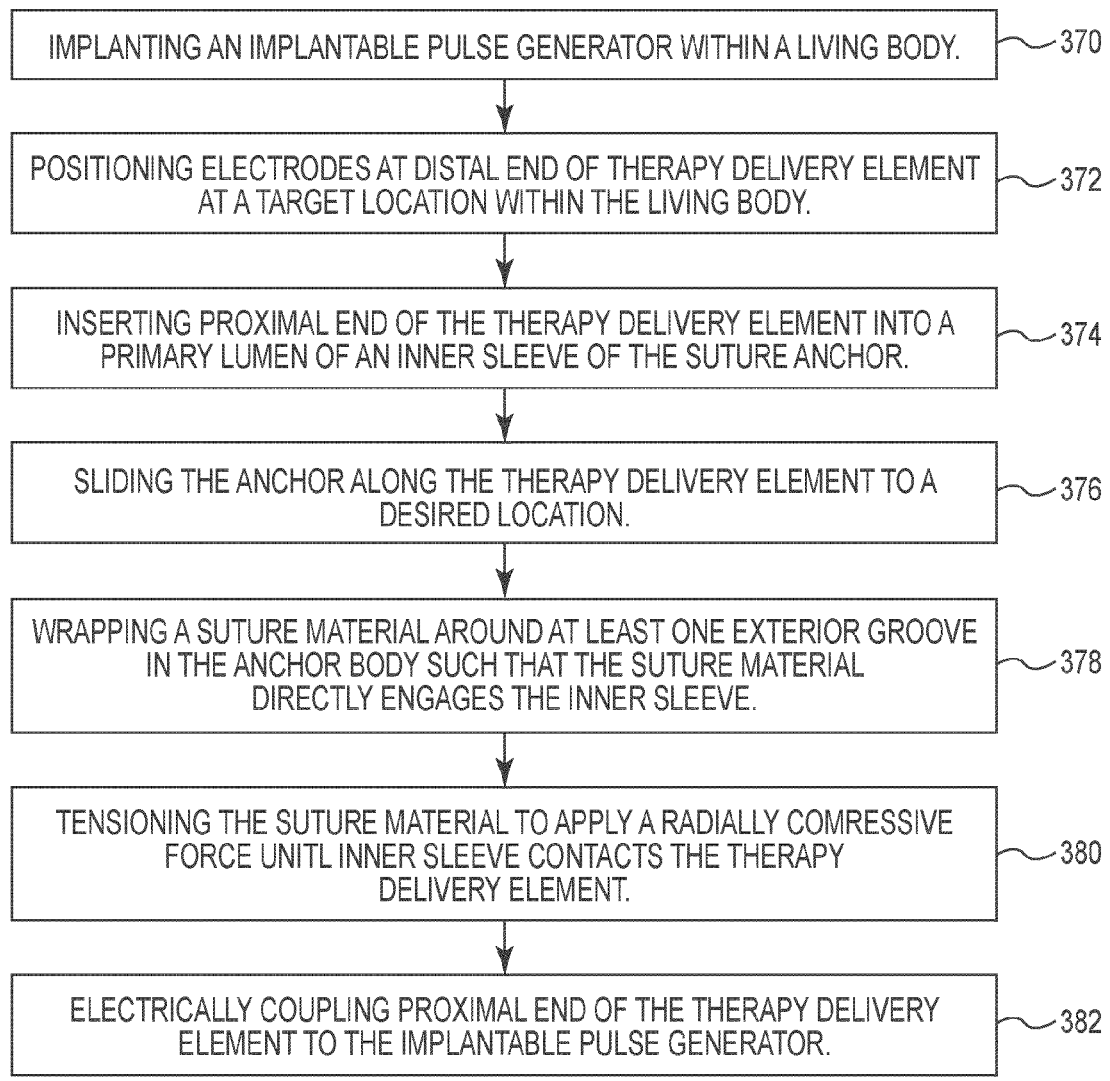
FIG. 15 is a flow diagram of an alternate method of implanting a neurostimulation system within a living body in accordance with an embodiment of the present disclosure.

FIG. 15 is an alternate flow diagram of a method of implanting a neurostimulation system within a living body. The method includes the steps of implanting an implantable pulse generator within the living body (370). Electrodes at a distal end of a therapy delivery element are positioned at a target location within the living body (372). A proximal end of the therapy delivery element is inserted into a primary lumen of an inner sleeve of a suture anchor (374). The suture anchor is slid along the therapy delivery element to a desired location (376). Suture material is wrapped around at least one exterior groove in the anchor body such that the suture material directly engages the inner sleeve (378). Suture material wrapped around the suture anchor is tensioned to apply a radial compression force until inner sleeve contacts the therapy delivery element (380). The proximal end of the therapy delivery element is electrically coupled to the implantable pulse generator (382).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A suture anchor for securing a therapy delivery element in a desired location within a living body using a suture material, the suture anchor comprising:
    an inner sleeve comprising a primary lumen sized to receive the therapy delivery element, the inner sleeve comprising a compliant material having a first durometer;
    an anchor body extending around at least a portion of the inner sleeve and comprising a portion of the primary lumen, the anchor body comprising a compliant material having a second durometer less than the first durometer; and
    at least one exterior suture groove in the anchor body adapted to receive the suture material, the exterior suture groove extending substantially to the inner sleeve so that the suture material engages directly with the inner sleeve.

2. The suture anchor of claim 1, wherein the first durometer has a shore hardness ranging between 65 to 105 measured according to ASTM D2240 type A.

3. The suture anchor of claim 1, wherein the first durometer has a shore hardness ranging between 75 to 95 measured according to ASTM D2240 type A.

4. The suture anchor of claim 1, wherein the first durometer has a shore hardness ranging between 80 to 90 measured according to ASTM D2240 type A.

5. The suture anchor of claim 1, wherein the second durometer has a shore hardness ranging between 30 to 80 measured according to ASTM D2240 type A.

6. The suture anchor of claim 1, wherein the second durometer has a shore hardness ranging between 40 to 70 measured according to ASTM D2240 type A.

7. The suture anchor of claim 1, wherein the second durometer has a shore hardness ranging between 50 to 60 measured according to ASTM D2240 type A.

8. The suture anchor of claim 1, wherein the inner sleeve comprises:
   an outer layer comprising a material having the first durometer; and
   an inner layer comprising a material having a third durometer less than the first durometer.

9. The suture anchor of claim 8, wherein the third durometer has a shore hardness ranging between 25 to 30 measured according to ASTM D2240 type A.

10. The suture anchor of claim 8, wherein the third durometer has a shore hardness ranging between 20 to 35 measured according to ASTM D2240 type A.

11. The suture anchor of claim 8, wherein the third durometer has a shore hardness ranging between 15 to 40 measured according to ASTM D2240 type A.

12. The suture anchor of claim 1, comprising a reinforcing structure integrated with the inner sleeve, the reinforcing structure comprises one of a coil, a braid, a tube, or a woven component.

13. The suture anchor of claim 1, comprising a deformable insert located in the primary lumen of the inner sleeve.

14. The suture anchor of claim 1, comprising an insert located in the inner sleeve, the insert comprising:
   a pair of fixed rings located at opposite ends of the insert;
   at least one beam directly connecting the pair of fixed rings; and
   a plurality of beams indirectly connecting the pair of fixed rings.

15. The suture anchor of claim 14, wherein the insert comprises a material that plastically deforms in response to a radially inward force.

16. The suture anchor of claim 1, comprising the suture material located in the suture groove tensioned to apply a radial compression force that engages the inner sleeve with the therapy delivery element.

17. The suture anchor of claim 1, comprising the suture material located in the suture groove tensioned to apply a radial compression force, the inner sleeve spreading the radial compression force along a greater surface area of the therapy delivery element.

18. The suture anchor of claim 1, comprising the suture material configured in a self-locking compression knot located in the suture groove, the suture material comprising distal ends adapted to receive a tension force that is transmitted as a radial compression force to deform the inner sleeve to engage with the therapy delivery element.

19. A suture anchor for securing a therapy delivery element with respect to a living body using a suture material, the suture anchor comprising:
   an inner sleeve including a primary lumen sized to receive the therapy delivery element, the inner sleeve including a first material including a first durometer;
   an anchor body extending around at least a portion of the inner sleeve and including a portion of the primary lumen, the anchor body including a second material including a second durometer less than the first durometer; and
   at least one exterior suture groove in the anchor body configured to receive the suture material, the exterior suture groove extending to the inner sleeve so that the suture material engages directly with the inner sleeve, wherein:
      the first durometer of the first material provides a protective layer to inhibit damage to the therapy delivery element from over-tightening of the suture material; and
      the second durometer of the second material provides a slip-resistant surface for gripping the therapy delivery element.

20. The suture anchor of claim 19, wherein the inner sleeve includes a reinforcing structure.

21. The suture anchor of claim 19, wherein the inner sleeve includes:
   an outer layer including the first material including the first durometer; and
   an inner layer including a third material including a third durometer less than the first durometer.

22. The suture anchor of claim 21, wherein a reinforcing structure is disposed between the inner layer and the outer layer of the inner sleeve.

23. The suture anchor of claim 19, comprising a deformable insert disposed within the primary lumen of the inner sleeve.

24. The suture anchor of claim 19, comprising an insert disposed within the inner sleeve, the insert including:
   a pair of fixed rings located at opposite ends of the insert;
   at least one beam directly connecting the pair of fixed rings; and
   a plurality of beams indirectly connecting the pair of fixed rings.

25. The suture anchor of claim 24, wherein the insert includes a material that plastically deforms in response to a radially inward force.

26. The suture anchor of claim 19, comprising the suture material disposed within the suture groove, the suture material configured to be tensioned to apply a radial compression force that engages the inner sleeve with the therapy delivery element.

27. A suture anchor for securing a therapy delivery element with respect to a living body using a suture material, the suture anchor comprising:
   an inner sleeve including a primary lumen sized to receive the therapy delivery element, the inner sleeve including:
      an outer layer including a first material including a first durometer; and
      an inner layer including a third material including a third durometer less than the first durometer;
   an anchor body extending around at least a portion of the inner sleeve and including a portion of the primary lumen, the anchor body including a second material including a second durometer less than the first durometer;
   a reinforcing structure disposed between the inner layer and the outer layer of the inner sleeve; and
   at least one exterior suture groove in the anchor body configured to receive the suture material, the exterior suture groove extending to the inner sleeve so that the suture material engages directly with the inner sleeve, wherein:
      the first durometer of the outer layer of the inner sleeve and the reinforcing layer provide a protective layer to inhibit damage to the therapy delivery element from over-tightening of the suture material; and the second durometer of the anchor body and the third durometer of the inner layer of the inner sleeve provide a slip-resistant surface for gripping the therapy delivery element.

28. The suture anchor of claim 27, comprising a deformable insert disposed within the primary lumen of the inner sleeve.

29. The suture anchor of claim 27, comprising an insert disposed within the inner sleeve, the insert including:
   a pair of fixed rings located at opposite ends of the insert;
   at least one beam directly connecting the pair of fixed rings; and
   a plurality of beams indirectly connecting the pair of fixed rings.

30. The suture anchor of claim 27, wherein the at least one exterior suture groove extends completely circumferentially around the anchor body.

\* \* \* \* \*